United States Patent
Barcikowski et al.

(10) Patent No.: US 9,243,089 B2
(45) Date of Patent: Jan. 26, 2016

(54) COPOLYMER-MODIFIED NANOPARTICLES, ESPECIALLY FOR USE IN MEDICAL ARTICLES

(76) Inventors: Stephan Barcikowski, Essen (DE); Christin Menneking, Bonn (DE); Markus Klapper, Mainz (DE); Klaus Müllen, Köln (DE); Michael Hoffmann, Germering (DE); Simon Stelzig, Radolfzell (DE); Dennis Langanke, Kassel (DE); Helmut Goldmann, Kassel (DE)

( * ) Notice: Subject to any disclaimer, the term of this patent is extended or adjusted under 35 U.S.C. 154(b) by 74 days.

(21) Appl. No.: 13/641,962

(22) PCT Filed: Apr. 19, 2011

(86) PCT No.: PCT/EP2011/056251
§ 371 (c)(1),
(2), (4) Date: Feb. 8, 2013

(87) PCT Pub. No.: WO2011/131681
PCT Pub. Date: Oct. 27, 2011

(65) Prior Publication Data
US 2013/0197628 A1    Aug. 1, 2013

(30) Foreign Application Priority Data
Apr. 20, 2010  (DE) .......................... 10 2010 018 073

(51) Int. Cl.
| | | |
|---|---|---|
| C08F 212/08 | (2006.01) |
| C08F 220/18 | (2006.01) |
| C08F 214/18 | (2006.01) |
| A61F 2/06 | (2013.01) |
| B01J 13/02 | (2006.01) |
| C08F 112/14 | (2006.01) |
| B23K 26/00 | (2014.01) |
| C08F 220/68 | (2006.01) |
| C08F 14/18 | (2006.01) |

(52) U.S. Cl.
CPC ................ *C08F 112/14* (2013.01); *A61F 2/06* (2013.01); *B01J 13/02* (2013.01); *B23K 26/0066* (2013.01); *C08F 220/68* (2013.01); *C08F 14/18* (2013.01); *C08F 212/08* (2013.01); *C08F 214/18* (2013.01); *C08F 2220/1833* (2013.01); *Y10S 977/773* (2013.01)

(58) Field of Classification Search
None
See application file for complete search history.

(56) References Cited

U.S. PATENT DOCUMENTS

| 2007/0154709 A1* | 7/2007 | Koch et al. .................... 428/379 |
| 2009/0110719 A1* | 4/2009 | Roy et al. ...................... 424/450 |
| 2009/0163994 A1* | 6/2009 | Quigley et al. .............. 623/1.15 |
| 2011/0189695 A1* | 8/2011 | Barcikowski et al. ......... 435/7.2 |

FOREIGN PATENT DOCUMENTS

| DE | 197 03 208 A1 | 8/1998 |
| DE | 10 2005 019 391 A1 | 10/2006 |
| DE | 10 2007 005 817 A1 | 8/2008 |
| EP | 1 708 963 B1 | 10/2006 |
| WO | 2005/070820 A1 | 8/2005 |
| WO | 2005/070979 A1 | 8/2005 |
| WO | 2008/095645 A3 | 8/2008 |
| WO | 2010/007117 A1 | 1/2010 |
| WO | WO 2010007117 A1 * | 1/2010 |

OTHER PUBLICATIONS

SH Stelzig, C Menneking, MS Hoffmann, K Eisele, S Barcikowski, M Klapper, K Mullen. "Compatibilization of laser generated antibacterial Ag- and Cu-nanoparticles for perfluorinated implant materials." European Polymer Journal, vol. 47, 2011, pp. 662-667.*

Jewrajka, S.K. et al., "Block Copolymer Mediated Synthesis of Amphiphilic Gold Nanoparticles in Water and an Aqueous Tetrahydrofuran Medium: An Approach for the Preparation of Polymer-Gold Nanocomposites," *Polym Chem*, 2006, vol. 44, pp. 1841-1854.

Besner, S. et al., "Synthesis of Size-Tunable Polymer-Protected Gold Nanoparticles by Femtosecond Laser-Based Ablation and Seed Growth," *J. Phys. Chem. C*, 2009, vol. 113, pp. 9526-9531.

Bao, H. et al., "Preparation of Magnetic Nanoparticles Modified by Amphiphilic Copolymers," *Materials Letters*, 2006, vol. 60, pp. 1267-2170.

Menneking, V.C. et al., "Rapid Nanomaterial Manufacturing—Funktionstragende Nanopartikel in Materialien und auf Oberflächen," *Galvanotechnik*, 2009, vol. 1, pp. 56-26.

Barcikowski, S. et al., "Properties of Nanoparticles Generated during Femtosecond Laser Machining in Air and Water," *Appl. Phys.*, 2007, vol. A, No. 87, pp. 47-55.

Petersen, S. et al., "In Situ Bioconjugation: Single Step Approach to Tailored Nanoparticle-Bioconjugates by Ultrashort Pulsed Laser Ablation," *Adv. Funct. Mater.*, 2009, vol. 19, pp. 1165-1172.

Petersen, S. et al., "In Situ Bioconjugation—Novel Laser Based Approach to Pure Nanoparticle-Conjugates," *Applied Surface Science*, 2009, vol. 255, pp. 5435-5438.

Hahn, A. et al., "Influences on Nanoparticle Production during Pulsed Laser Ablation," *JLMN—Journal of Laser Micro/Nanoengineering*, 2008, vol. 3, No. 2, pp. 73-77.

Compagnini, G. et al., "Synthesis of Gold Colloids by Laser Ablation in Thiol-Alkane Solutions," *J. Mater. Res.*, Oct. 2004, vol. 19, No. 10, pp. 2795-2798.

Sylvestre, J.-P. et al., "Surface Chemistry of Gold Nanoparticles Produced by Laser Ablation in Aqueous Media," *J. Phys. Chem. B*, 2004, vol. 108, pp. 16864-16869.

(Continued)

*Primary Examiner* — Isaac Shomer
(74) *Attorney, Agent, or Firm* — DLA Piper LLP (US)

(57) ABSTRACT

Copolymer-modified nanoparticles produced by a process in which nanoparticles are ablated by laser radiation from a surface of a substrate in a liquid include an amphiphilic copolymer.

10 Claims, No Drawings

(56) References Cited

OTHER PUBLICATIONS

Sylvestre, J-P. et al., "Stabilization and Size Control of Gold Nanoparticles during Laser Ablation in Aqueous Cyclodextrins," *J. Am. Chem. Soc.*, 2004, vol. 126, No. 23, pp. 7176-7177.

Amendola, V. et al., "Free Silver Nanoparticles Synthesized by Laser Ablation in Organic Solvents and Their Easy Functionalization," *Langmuir*, 2007, vol. 23, pp. 6766-6770.

Barcikowski, S. et al., "Nanocomposite Manufacturing Using Ultrashort-Pulsed Laser Ablation in Solvents and Monomers," *Polimery*, 2008, vol. 53, No. 9, pp. 657-662.

Amendola, V. et al., "Laser Ablation Synthesis in Solution and Size Manipulation of Noble Metal Nanoparticles," *Phys. Chem. Chem. Phys.*, 2009, vol. 11, pp. 3805-3821.

* cited by examiner

COPOLYMER-MODIFIED NANOPARTICLES, ESPECIALLY FOR USE IN MEDICAL ARTICLES

RELATED APPLICATIONS

This is a §371 of International Application No. PCT/EP2011/056251, with an international filing date of Apr. 19, 2011 (WO 2011/131681 A1, published Oct. 27, 2011), which is based on German Patent Application No. 10 2010 018 073.4, filed Apr. 20, 2010, the subject matter of which is incorporated herein by reference.

TECHNICAL FIELD

This disclosure relates to copolymer-modified nanoparticles, to a process for production thereof, and to applications for the copolymer-modified nanoparticles, especially in medical articles.

BACKGROUND

The use of nanoparticles has enormous potential, in particular for the development of new polymer-based medical products.

Conventional processes for producing nanoparticles are usually based on chemical production methods. Such methods generate nanoparticles typically by conversion of suitable precursor compounds. For example, the precursor compounds can be reacted with an acid, an alkali, a reducing agent or oxidizing agent to give nanoparticles.

An elegant method for production of nanoparticles is that of laser ablation (material removal by laser) in liquids (Amendola et al.: Laser ablation synthesis in solution and size manipulation of noble metal nanoparticles; Phys. Chem. Chem. Phys. 2009, 11, 3805-3821 and Barcikowski et al.: Nanocomposite manufacturing using ultrashort-pulsed laser ablation in solvents and monomers; Polimery 2008, 53, nr 9). Nanoparticles are generated by bombarding substrates immersed into liquid-filled sample vessels with laser radiation. The laser bombardment causes material removal from the substrate surface. The nanoparticles generated are generally the result of nucleation and coalescence phenomena within cavitation bubbles formed above the substrate surface as a result of laser irradiation.

A central problem in generating nanoparticles relates to the agglomeration tendency thereof, as a result of which the further use thereof, especially incorporation thereof into polymeric materials, can be limited in terms of maximum homogeneity of dispersion. An additional factor is that a rise in agglomeration is generally recorded when nanoparticles are subjected to conditions as typically employed in industrial shaping processes, for example, extrusion processes. This is especially true with regard to polymeric materials with high processing temperatures.

One approach to suppressing the unwanted agglomeration tendency of nanoparticles, for example, to achieve maximum homogeneity of "nano-functionalization," consists of a surface modification of the nanoparticles. However, a difficulty is in developing a suitable surface modification. For instance, in the case of a simple hydrophobic modification of nanoparticle surfaces, there is the risk of separation of nanoparticles and polymer. In the case of a slight surface modification, in contrast, there is the risk that the nanoparticles form unwanted agglomerates, as a result of which a homogeneous "nano-functionalization" likewise cannot be achieved.

WO 2005/070979 A1 describes a chemical production process, based on so-called "emulsion" technology, for polymer-modified nanoparticles.

Chemical production methods for nanoparticles are, however, afflicted with certain disadvantages. For instance, the particle size and the particle size distribution can frequently be controlled only with very great difficulty under the particular chemical conditions. Furthermore; generally time-consuming and costly purification and disposal measures are required for unconverted precursor compounds, reagents and by-products which form. However, impurities are unacceptable especially with regard to medical applications.

The use of laser-generated nanoparticles for production of biologically active devices is known from DE 10 2007 005 817 A1.

It could therefore be helpful to provide modified nanoparticles which avoid known shortcomings and can especially be dispersed very substantially uniformly and homogeneously in polymers.

SUMMARY

We provide copolymer-modified nanoparticles produced by a process in which nanoparticles are ablated by laser radiation from a surface of a substrate in a liquid including an amphiphilic copolymer.

We also provide a process for producing copolymer-modified nanoparticles including ablating nanoparticles by laser radiation from a surface of a substrate in a liquid including an amphiphilic random copolymer.

We further provide a polymer including the copolymer-modified nanoparticles, wherein the polymer is a fluoropolymer selected from the group consisting of poly(2,3,4,5,6-pentafluorostyrene), poly(1H,1H-heptafluorobutyl methacrylate), perfluoroxyalkyl vinyl ether, poly(chlorotrifluoroethylene), polyhexafluoropropylene, polyvinylidene difluoride, polytetrafluoroethylene, homopolymers thereof, copolymers thereof and combinations or blends thereof.

We still further provide a semifinished product, finished product or end product including nanoparticles modified with an amphiphilic random copolymer including the copolymer-modified nanoparticles.

We further yet provide a medical article including nanoparticles modified with an amphiphilic random copolymer including the copolymer-modified nanoparticles.

DETAILED DESCRIPTION

Our nanoparticles are copolymer-modified nanoparticles produced or producible (obtained or obtainable) by a process in which nanoparticles are ablated (removed) by laser radiation from the surface of at least one, especially one, substrate in a liquid which comprises an amphiphilic, preferably random copolymer.

An amphiphilic copolymer shall be understood to mean a polymer based on at least two different monomer units, at least one monomer unit being a hydrophilic monomer unit and at least one further monomer unit being a hydrophobic and/or fluorophilic monomer unit.

A hydrophilic monomer unit shall preferably be understood to mean a monomer unit which has a hydrophilic side group. With regard to the hydrophilic side groups useful in principle, reference is made to the details still to be given on this subject hereinafter.

A hydrophobic or fluorophilic monomer unit shall preferably be understood to mean a monomer unit with a hydrophobic or fluorophilic side group. With regard to hydrophobic or fluorophilic side groups useful in principle, reference is made to the details still to be given on this subject hereinafter.

It has been found that, surprisingly, nanoparticles generated by laser ablation (material removal by laser) can be obtained in essentially agglomerate-free form in liquids when the laser ablation is performed in the presence of an amphiphilic and preferably random copolymer present in the liquid. The nanoparticles can thus be produced particularly advantageously in a "one-pot process."

The reason for the lack of or greatly reduced agglomeration tendency is based on a surface modification of the nanoparticles, as a result of which the amphiphilic copolymer adds onto the surface of nanoparticles to form copolymer-modified nanoparticles. This results in mutual screening of the nanoparticles, as a result of which the tendency thereof to form agglomerates is lowered or suppressed.

In general, modification of the nanoparticles is based on noncovalent, especially adsorptive, bonds between the nanoparticles and the amphiphilic copolymer. The bonds are preferably based on Lewis acceptor and Lewis donor interactions. The nanoparticles here generally have Lewis acceptor character. The amphiphilic copolymer preferably has donating atom groups generally present in the side chains of the copolymer. The amphiphilic copolymer therefore preferably has Lewis donor character.

A donating atom group (donor group) shall be understood to mean an atom group with at least one heteroatom, with at least one free electron pair of the heteroatom able to interact with a Lewis-acidic particle. Suitable donating atom groups can be selected from the group consisting of hydroxyl groups, ether groups, amino groups, amine groups, imine groups, oxime groups, diol groups, thioether groups, acyl groups, formyl groups, keto groups, carboxyl or carboxylate groups, amide groups, sulfo or sulfonate groups, phosphoric acid or phosphate groups, phosphonic acid or phosphonate groups, and combinations thereof.

Preferably, the nanoparticles are at least partially, preferably fully, coated with the amphiphilic copolymer.

The copolymer-modified nanoparticles more preferably have a core-shell structure ("core-shell particles"), in which case the nanoparticles form the core and the copolymer forms the shell of the structure.

Nanoparticles shall be understood to mean particles with a dimension in the submicrometer range, especially with a dimension of ≤100 nm. Due to their small size, nanoparticles have a comparatively large surface area, through which they can release, for example, active ingredients (in the case of metallic nanoparticles, for example, ions). At the same time, the nanoparticles constitute, due to their volume, a considerable reservoir for active ingredients to be released.

The nanoparticles preferably comprise an inorganic material, especially a metal, a metal salt, especially a metal oxide, a metal alloy, a semi-metal, a ceramic, an organic material or a combination thereof.

The nanoparticles preferably comprise biologically active materials. Biologically active materials shall be understood to mean materials which can display advantageous effects in a biological system, for example, in the body of a patient, in particular from a medical point of view, especially a diagnostic and/or therapeutic point of view. For example, the nanoparticles may comprise antimicrobial, especially antibiotic, disinfecting, inflammation-inhibiting, antithrombogenic, cell growth-promoting, cell-differentiating, cell-recruiting, cell-adhering materials or substances or combinations thereof.

The nanoparticles more preferably comprise antimicrobially active metals, metal salts, metal alloys or combinations thereof.

In addition, the nanoparticles may, however, also comprise materials with other properties, for example, self-cleaning properties (e.g., titanium dioxide), electrical conductivity properties, antistatic properties or UV-protective properties (e.g., zinc oxide).

The nanoparticles may comprise a metal selected from the group consisting of magnesium, aluminium, copper, zinc, tantalum, titanium, cobalt, iron, palladium, platinum, iridium, silver, gold, salts thereof, especially oxides thereof, and combinations, especially alloys, thereof.

The nanoparticles may also comprise metal alloys selected from the group consisting of nickel-titanium alloys (NiTi), iron-nickel alloys (FeNi), gold-silver alloys (AuAg), silver-copper alloys (AgCu) and combinations thereof.

Examples of ceramic-comprising nanoparticles can be selected from the group consisting of zirconium dioxide ($ZrO_2$), aluminium oxide ($Al_2O_3$), silicon oxide ($SiO_2$), titanium carbide, tungsten carbide (WC), boron nitride (BN) and combinations thereof.

The nanoparticles may also consist of one of the materials or material combinations described above.

In addition, the nanoparticles themselves may have a spherical, spheroidal or irregular, for example, polygonal, form. Preferably, the nanoparticles themselves (without the copolymer modification) have a mean particle size, preferably determined by dynamic light scattering or transmission electron microscopy of 1 to 100 nm, especially 1 to 50 nm, preferably 2 to 40 nm, more preferably 3 to 30 nm, especially preferably 5 to 20 nm.

The copolymer-modified nanoparticles may be present in solid form or as a solid. More particularly, the copolymer-modified nanoparticles may be present as a particulate solid, for example, as a dry chemical, powder, granules or the like. Since the copolymer-modified nanoparticles can also form films themselves, it is also possible that the copolymer-modified nanoparticles are in the form of a film or foil. In the example described in this paragraph, the copolymer-modified nanoparticles may have a proportion of 0.1 to 100% by weight, especially 0.5 to 40% by weight, preferably 1 to 5% by weight, based on the total weight of the particular configuration (powder, granules, film and the like). It may therefore quite possibly be preferred that the copolymer-modified nanoparticles are also present in the form of pure material (proportion of 100% by weight).

The copolymer-modified nanoparticles may be present together with a liquid dispersant in the form of a dispersion, optionally a dispersion in gel form. The copolymer-modified nanoparticles are preferably present in a dispersion as colloids, preferably in homogeneous distribution. Furthermore, the copolymer-modified nanoparticles may be present as a gel, in particular hydrogel. With regard to further features and advantages of the dispersion, especially with regard to suitable dispersants, reference is made completely to the present description.

The amphiphilic copolymer preferably has a weight-average molar mass of 1000 to 1 000 000 g/mol, especially 1000 to 500 000 g/mol, preferably 3000 to 100 000 g/mol.

The amphiphilic copolymer may be soluble in organic solvents or mixtures thereof, especially in ethyl acetate, methanol, ethanol, isopropanol, acetone, dioxane, THF, DMF, DMSO, acetonitrile, 4-butyrolactone, dichloromethane, chloroform, carbon tetrachloride, toluene, N-methyl-2-pyrrolidone, perfluorinated solvents, for example, perfluoromethylcyclohexane, perfluoroalkanes, aromatic perfluorinated solvents, or mixtures thereof.

Preferably, the amphiphilic copolymer is a fluorophilic or fluorinated copolymer. The copolymer preferably has fluorophilic side groups, i.e., side groups whose hydrogen atoms have been replaced partly or fully (completely) by fluorine atoms. More preferably, the copolymer has perfluorinated side groups, in particular selected from the group consisting of perfluorinated alkyl groups, perfluorinated alkenyl groups, perfluorinated alkinyl groups, perfluorinated aryl groups and combinations thereof. Perfluorinated alkyl groups are especially preferred. A perfluorinated side group shall be understood to mean a side group whose hydrogen atoms have been fully (completely) replaced by fluorine atoms.

The copolymer may comprise at least one repeat monomer unit, preferably two repeat monomer units, with hydrophobic and/or fluorophilic side groups and at least one, preferably one, repeat monomer unit with hydrophilic side groups. The weight ratio of monomer units with hydrophobic and/or fluorophilic side groups to monomer units with hydrophilic side groups may be 95:5 to 10:90, especially 95:5 to 30:70, preferably 90:10 to 50:50. The monomer units may in principle also be macromonomers, preference being given to polyolefins, polyacrylates and/or polyethers as macromonomers.

More particularly, monomer units with hydrophobic and/or fluorophilic side groups may have a proportion of 10 to 98 mol %, preferably 50 to 95 mol %, more preferably 75 to 90 mol %, based on 100 mol % of the copolymer.

Monomer units with hydrophilic side groups preferably have a proportion of 2 to 90 mol %, especially 5 to 50 mol %, preferably 10 to 25 mol %, based on 100 mol % of the copolymer.

Further preferably, the amphiphilic copolymer has hydrophobic and/or fluorophilic side groups selected from the group consisting of cyclic, branched and/or unbranched alkyl radicals, alkenyl radicals, alkinyl radicals, haloalkyl radicals, haloalkenyl radicals, haloalkinyl radicals, alkoxy radicals, particularly alkoxy alkyl radicals, alkoxy alkenyl radicals and/or alkoxy alkinyl radicals, aryl radicals and combinations thereof, where preferably one or more hydrogen atoms, especially all hydrogen atoms, of the side groups are replaced by fluorine atoms.

The amphiphilic copolymer may have hydrophilic side groups which preferably have a hydroxyl radical, hydroxyalkyl radical, especially hydroxymethyl radical, hydroxyethyl radical, hydroxypropyl radical, amino radical, amine radical, ammonium radical, phosphoric acid or phosphate radical, phosphonic acid or phosphonate radical, sulfo or sulfonate radical, carboxyl or carboxylate radical, polyol radical, polyether radical, betaine radical or combinations thereof.

The copolymer, especially the backbone thereof, is preferably derived or made from poly-para-hydroxystyrene, polymethacrylate, polyacrylates, polysiloxanes or combinations thereof.

Particularly preferably, the amphiphilic copolymer corresponds to the Formula I:

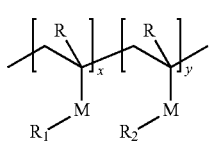

Formula I where
x and y are each a molar proportion of monomer units in the copolymer,
R is a hydrogen atom or an alkyl radical, M is an aryl radical and/or an acyl radical or a radical containing an acyl radical, formyl radical, keto radical, carboxyl radical or amide radical, $R_1$ is a hydrophobic or fluorophilic side group, a cyclic, branched and/or unbranched alkyl, alkenyl, alkinyl, haloalkyl, haloalkenyl, haloalkinyl, alkoxy, particularly alkoxyalkyl, alkoxyalkenyl and/or alkoxyalkinyl, and/or aryl radical, in which one or more hydrogen atoms are replaced by fluorine atoms, and $R_2$ is a hydrophilic side group, comprising a hydroxyl radical, hydroxyalkyl radical, hydroxyethyl radical, hydroxypropyl radical, amino radical, amine radical, ammonium radical, phosphoric acid or phosphate radical, phosphonic acid or phosphonate radical, sulfo or sulfonate radical, carboxyl or carboxylate radical, polyol radical, betaine radical, polyether radical or combinations thereof.

x may be 10 to 98 mol %, preferably 50 to 95 mol %, more preferably 75 to 90 mol %, and y may be 2 to 90 mol %, preferably 5 to 50 mol %, more preferably 10 to 25 mol %, based in each case on 100 mol % of the copolymer with the Formula I.

The side group $R_1$ may comprise a carbon chain with at least three carbon atoms, in particular a carbon chain having three to eight carbon atoms. The carbon chain may be a branched, a cyclic or an unbranched carbon chain.

The side group $R_1$ may be selected from the group consisting of cyclic alkyl radicals, branched alkyl radicals, unbranched alkyl radicals and combinations thereof, where the alkyl radicals preferably have a carbon chain with at least three carbon atoms. The side group $R_1$ preferably has alkyl radicals selected from the group consisting of propyl radical, isopropyl radical, butyl radical, isobutyl radical, pentyl radical, isopentyl radical, hexyl radical, isohexyl radical, heptyl radical, isoheptyl radical, octyl radical, isooctyl radical and combinations thereof.

The amphiphilic copolymer may be a terpolymer, i.e., a polymer composed of three different, preferably repeat monomer units. The monomer units of the terpolymer are preferably selected from the group consisting of hydrophobic, fluorophilic and/or hydrophilic monomer units. More preferably, two monomer units have hydrophobic and/or fluorophilic side groups and one monomer unit has hydrophilic side groups.

More preferably, the amphiphilic copolymer has the Formula II below:

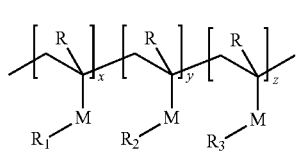

Formula II where
x, y and z are each a molar proportion of monomer units in the copolymer,
R is a hydrogen atom and/or an alkyl radical,
M is an aryl radical and/or an acyl radical or a radical containing an acyl radical, formyl radical, keto radical, carboxyl radical or amide radical,
$R_1$ and $R_2$ are the same or different, where
$R_1$ and/or $R_2$ are each a hydrophobic or fluorophilic side group, selected from the group consisting of a cyclic, branched and/or unbranched alkyl, alkenyl, alkinyl, haloalkyl, haloalkenyl, haloalkinyl, alkoxy, particularly alkoxyalkyl, alkoxyalkenyl and/or alkoxyalkinyl, and/or aryl radical, in which one or more hydrogen atoms are replaced by fluorine atoms, and/or $R_1$ and/or $R_2$ are each a hydrophilic side group, comprising a hydroxyl radical, hydroxyalkyl radical, hydroxyethyl radical, hydroxypropyl radical, amino radical, amine radical, ammonium radical, phosphoric acid or phosphate radical, phosphonic acid or phosphonate radical, sulfo or sulfonate radical, carboxyl or carboxylate radical, polyol radical, betaine radical and/or polyether radical, and $R_3$ is a hydrophobic and/or fluorophilic side group selected from the group consisting of a cyclic, branched and/or unbranched alkyl, alkenyl, alkinyl, haloalkyl, haloalkenyl, haloalkinyl, alkoxy, particularly alkoxyalkyl, alkoxyalkenyl and/or alkoxyalkinyl, and/or aryl radical, in which one or more hydrogen atoms are replaced by fluorine atoms.

x may be 0.1 to 99 mol %, especially 50 to 95 mol %, preferably 80 to 95 mol %, y may be 0.1 to 50 mol %, especially 5 to 35 mol %, preferably 5 to 10 mol %, and z may be 0.1 to 99 mol %, especially 5 to 20 mol %, preferably 5 to 10 mol %, based in each case on 100 mol % of the copolymer represented by the Formula II, and especially with the proviso that the sum of x, y and z corresponds to 100 mol % of the copolymer (x+y+z=100 mol %).

More particularly, x may be 0.1 to 99 mol %, especially 50 to 95 mol %, preferably 80 to 95 mol %, based on 100 mol % of the copolymer represented by the Formula II, and x and y together may be 99.9 to 1 mol %, especially 50 to 5 mol %, preferably 20 to 5 mol %, based on 100 mol % of the copolymer represented by the Formula II.

The side groups $R_1$, $R_2$ and/or $R_3$ may comprise a carbon chain with at least three carbon atoms. More specifically, the side groups $R_1$, $R_2$ and/or $R_3$ may have a carbon chain with three to eight carbon atoms.

The side groups $R_1$, $R_2$ and/or $R_3$ may be selected from the group consisting of cyclic alkyl radicals, branched alkyl radicals, unbranched alkyl radicals and combinations thereof, where the alkyl radicals preferably have a carbon chain with at least three carbon atoms. The side groups $R_1$, $R_2$ and/or $R_3$ preferably have alkyl radicals selected from the group consisting of propyl radical, isopropyl radical, butyl radical, isobutyl radical, pentyl radical, isopentyl radical, hexyl radical, isohexyl radical, heptyl radical, isoheptyl radical, octyl radical, isooctyl radical and combinations thereof.

Preferably, the copolymer-modified nanoparticles are present in or within a medical article. Moreover, the copolymer-modified nanoparticles may be present on a surface, in particular an exterior surface, of a medical article, preferably in the form of a coating or, as an alternative, being a component of such a coating. The medical article is preferably a medical or surgical implant, more preferably a vascular, in particular arterial, prosthesis or graft. With regard to further features and advantages of the medical article, reference is made completely to the following description.

We also provide copolymer-modified nanoparticles, wherein the copolymer is an amphiphilic, preferably random copolymer. The copolymer preferably corresponds to the above-described Formula II.

To avoid unnecessary repetition, with regard to further features and advantages in respect of the copolymer-modified nanoparticles, especially in relation to the nanoparticles themselves and/or the amphiphilic copolymer, reference is made completely to the description above.

We further provide a process for producing or manufacturing copolymer-modified nanoparticles in which nanoparticles are ablated by laser radiation from the surface of at least one, especially one, substrate in a liquid which comprises an amphiphilic, preferably random copolymer.

The copolymer present in the liquid functionalizes or modifies the surfaces of the laser-ablated nanoparticles in situ ("in situ functionalization" or "in situ conjugation"). As a result, a dispersion is generally obtained, possibly a dispersion in the form of a gel in which the copolymer-modified nanoparticles are generally present as colloids, preferably in homogeneous and fine distribution. The dispersions obtained are particularly advantageously notable for exceptionally good storage stability.

The amphiphilic copolymer is preferably a copolymer or a mixture of copolymers, preferably a copolymer which corresponds to the Formula I or II or a mixture thereof.

Preferably, the nanoparticles are generated by pulsed laser radiation. It is particularly suitable to use short-pulse or ultrashort-pulse lasers, i.e., lasers with a pulse duration within the nanosecond, picosecond or femtosecond range. In the case of such (ultra)short laser pulses, the nanoparticles can particularly advantageously be obtained stochiometrically from the substrate because, due to the shortness of the pulse, thermal action on the substrate is locally limited. A further advantage is that a thermal influence on the liquid surrounding the substrate is avoided. The nanoparticles are preferably generated by quality-switched or mode-coupled lasers.

The wavelength of the laser radiation used for ablation or generation of nanoparticles is generally adapted to the absorption spectrum of the solvent and copolymer used, preferably such that the absorption of the copolymer and of the solvent is at a minimum. Suitable wavelengths may, for example, be 532 nm, 800 nm, 1030 nm or 1064 nm. In the case of use of ultrashort pulses, especially at intensities which lead to multiphoton absorption, the laser wavelength should be at least twice the absorption edge of the copolymer.

In general, the liquid used to perform the laser ablation is an organic solvent or a mixture of organic solvents. The liquid is preferably selected from the group consisting of ethyl acetate, methanol, ethanol, isopropanol, acetone, dioxane, THF, DMF, DMSO, acetonitrile, 4-butyrolactone, dichloromethane, chloroform, carbon tetrachloride, toluene, N-methyl-2-pyrrolidone, perfluorinated solvents, for example, perfluoromethylcyclohexane, perfluoroalkanes, aromatic perfluorinated solvents, and mixtures thereof.

The substrates used may be the materials already mentioned in connection with the nanoparticles in this description, especially metals and/or metal alloys. The substrates may appropriately have an even and preferably flat surface and can be configured, for example, in the form of sheets, slabs or the like. Alternatively, it is also possible to use wires with a diameter corresponding to the laser focus.

The nanoparticles may be ablated from the surface of two, three or more substrates, each of which may consist of a different material. In this way, it is particularly advantageously possible to produce copolymer-modified nanoparticles with different properties, for example, antimicrobial, inflammation-inhibiting, antithrombogenic and cell growth-promoting properties. In the case of more than two substrates, the laser can be conducted over the substrates by a suitable steering device in random sequence or repeatedly in a fixed, defined sequence. In this way, different nanoparticles can be generated simultaneously in principle, which especially also leads to very good mixing in the liquid.

After the material removal by laser has ended, the liquid, especially for further use of the copolymer-modified nanoparticles, for example, for incorporation into polymers, can be removed at least partly, for example, by applying a reduced pressure or vacuum. In this case, depending on the ablated nanoparticles and the amphiphilic copolymer used and/or the liquid used, dispersions in the form of gels can be obtained.

The laser ablation can also be undertaken in a flow chamber with or without recycling of the liquid, as a result of which, depending on the reaction regime, diluted or concentrated copolymer-modified nanoparticles can be obtained.

With regard to further features and advantages of the production process, especially in relation to the nanoparticles and/or the amphiphilic copolymer, reference is made completely to the description above.

We further provide a polymer which comprises copolymer-modified nanoparticles.

The copolymer-modified nanoparticles are preferably present in homogeneous distribution or embedded in a matrix or three-dimensional structure of the polymer. In other words, the polymer itself preferably serves as a matrix or a carrier for the copolymer-modified nanoparticles (matrix or carrier polymer).

The copolymer-modified nanoparticles may have a proportion of 0.1 to 99.8% by weight, preferably 0.5 to 40% by weight, more preferably 1 to 5% by weight, based on the total weight of the polymer.

The polymer itself is preferably a fluoropolymer or a fluorophilic polymer, i.e., a polymer whose hydrogen atoms are partly or fully (completely) replaced by fluorine atoms.

The polymer is preferably selected from the group consisting of poly(2,3,4,5,6-pentafluorostyrene), poly(1H,1H-heptafluorobutyl methacrylate), perfluoroxyalkyl vinyl ether, poly(chlorotrifluoroethylene), polytetrafluoropropylene, polyhexafluoropropylene, polyvinylidene difluoride, polytetrafluoroethylene, especially expanded polytetrafluoroethylene, homopolymers thereof, copolymers, in particular terpolymers, thereof and combinations or blends thereof.

Examples of suitable copolymers include copolymers selected from the group consisting of tetrafluoroethylene-perfluorovinyl ether copolymers, ethylene-tetrafluoroethylene copolymers, fluorinated ethylene-propylene copolymers, vinylidene difluoride-hexafluoropropylene copolymers, tetrafluoroethylene-hexafluoropropylene-vinylidene difluoride terpolymers, tetrafluoroethylene-perfluoromethyl vinyl ether copolymers, ethylene-chlorotrifluoroethylene copolymers and combinations thereof.

The fields of use for such polymers are extremely varied. In principle, the polymers can be used for production of moldings, semifinished products, finished products and/or end products, for example, pumps, tanks, vessels, filter housings, pipe valves, collars, flanges, tubes, linings for heat exchange, and for production of filter media.

In the automotive and aviation sectors, the polymers can be used, for example, for production of brake hoses, cooling water hoses, transmission and engine parts, sealing rings, sealing collars, sealing flanges, sealing discs, membranes for gasoline or fuel pumps, fuel hoses, tank hoses, outlet seals, and conductive fuel lines and/or gas discharge lines.

In wire and cable technology, it is possible with our polymers to produce, in particular, refractory, abrasion-resistant, wear-resistant and/or aging-resistant cables or sheathing for wires.

A further possible field of use of the polymers relates to the production of seals as typically used in radiators, air conditioning systems and transmission systems.

In the chemical industry, the polymers can be used, for example, for production of industrial hoses and pipe linings intended, for example, for the transport of chemicals. To improve corrosion resistance, it is, for example, also possible to coat pumps, tanks and/or valves with polymers.

Also possible is use of our polymers in the foods industry, for example, for production of running rollers and/or crank rollers.

To increase corrosion resistance, the polymers can also find use in the architectural sector, for example, in roofs, facades and decorative elements.

In addition, the polymers can be used for production of textiles, especially textile fibers, meshes or the like.

Quite generally, the polymers can be used in the textile industry, preferably for production of sports clothing and/or shoes.

A further possible field of use of the polymers relates to the use thereof for production of membranes, especially for food technology, fluid technology and/or pharmacy.

With regard to further features and advantages of the polymers, especially in relation to the copolymer-modified nanoparticles, the nanoparticles themselves and/or the amphiphilic copolymer, reference is made completely to the description above.

We further provide a coating composition, especially a polymeric coating composition, wherein the composition comprises copolymer-modified nanoparticles.

A coating composition shall be understood to mean a composition which is generally provided for coating of shaped bodies, for example, moldings, semifinished products, finished products and/or end products, for example, medical articles.

In the coating composition, the copolymer-modified nanoparticles may have a proportion of 0.1 to 99.8% by weight, preferably 0.5 to 40% by weight, more preferably 1 to 5% by weight, based on the total weight of the composition.

With regard to further features and advantages of the coating composition, especially in relation to the copolymer-modified nanoparticles, the nanoparticles themselves, the amphiphilic copolymer and/or possible polymers for the coating composition, reference is made completely to the description above.

A further aspect relates to a masterbatch comprising copolymer-modified nanoparticles. A masterbatch shall be understood to mean a polymer additive which may be present, for example, in the form of a powder or granules, the polymer additive having a content of the copolymer-modified nanoparticles preferably higher than in the final application, for example, in a molding, semifinished product, finished product or another shaped body, especially medical article. The masterbatch may optionally also be in the form of a dispersion, especially a dispersion in the form of a gel.

With regard to further features and advantages of the masterbatch or polymer additive, especially in relation to the copolymer-modified nanoparticles, the nanoparticles themselves, the amphiphilic copolymer and/or possible polymers for the masterbatch, reference is likewise made completely to the description above.

We further provide a liquid dispersion comprising a liquid dispersant, and nanoparticles modified with an amphiphilic, preferably random copolymer. The dispersion may optionally be present as a dispersion in the form of a gel. In other words, it may be preferred that the dispersion is a gel, in particular a hydrogel.

The dispersant is generally an organic solvent or a mixture of organic solvents which is preferably selected from the group consisting of ethyl acetate, methanol, ethanol, isopropanol, acetone, dioxane, THF, DMF, DMSO, acetonitrile, 4-butyrolactone, dichloromethane, chloroform, carbon tetrachloride, toluene, N-methyl-2-pyrrolidone, perfluorinated solvents, for example perfluoromethylcyclohexane, perfluoroalkanes, aromatic perfluorinated solvents, and mixtures thereof.

The copolymer-modified nanoparticles are preferably in colloidal distribution in the liquid dispersant.

The copolymer-modified nanoparticles are preferably copolymer-modified nanoparticles.

With regard to further features and advantages of the liquid dispersion, especially with regard to the copolymer-modified nanoparticles, the nanoparticles themselves and/or the amphiphilic copolymer, reference is likewise made to the details above.

We further provide a process for producing a polymer comprising copolymer-modified nanoparticles in which copolymer-modified nanoparticles are incorporated into a raw polymer.

A raw polymer shall preferably be understood to mean a polymer which is at least free of copolymer-modified nanoparticles.

Possible raw polymers include, for example, the polymers already mentioned.

Preferably, the copolymer-modified nanoparticles are incorporated into the raw polymer by producing a mixture of the raw polymer, the copolymer-modified nanoparticles and optionally additional additives. For this purpose, the raw polymer can be provided as a liquid dispersion, suspension, solution or melt. The copolymer-modified nanoparticles are preferably provided in the form of a liquid dispersion or in the form of a masterbatch.

With regard to further features and advantages of the process, especially in relation to the copolymer-modified nanoparticles, the nanoparticles themselves and/or the amphiphilic copolymer, reference is again made to the details given above.

We further provide a semifinished product, finished product (component prefabricated from raw material or semifinished product used in an end product without further processing) or end product comprising nanoparticles modified with an amphiphilic, preferably random copolymer, or a polymer comprising nanoparticles modified with an amphiphilic, preferably random copolymer. The copolymer-modified nanoparticles are preferably copolymer-modified nanoparticles.

Preferably, the copolymer-modified nanoparticles are present in a homogeneous dispersion in the semifinished product, finished product or end product. Alternatively, the semifinished product, finished product or end product may also have a coating with the copolymer-modified nanoparticles.

The copolymer-modified nanoparticles preferably have a proportion of 0.1 to 99.8% by weight, preferably 0.5 to 40% by weight, more preferably 1 to 5% by weight, based on the total weight of the semifinished product, finished product or end product.

With regard to further features and advantages of the semifinished product, finished product or end product, especially in relation to the copolymer-modified nanoparticles, the nanoparticles themselves and/or the amphiphilic copolymer, reference is made completely to the description so far.

In addition, we also provide a process for producing a semifinished product, finished product or end product, in which nanoparticles modified with an amphiphilic, preferably random copolymer, preferably copolymer-modified nanoparticles, are incorporated into a raw polymer and then the raw polymer is shaped together with the incorporated copolymer-modified nanoparticles to give a semifinished product, finished product or end product.

The raw polymer is preferably shaped together with the incorporated copolymer-modified nanoparticles by extrusion, especially strand extrusion, fiber extrusion or film extrusion, spinning, especially fiber spinning, pressing, especially hot pressing, punch pressing, especially micro punch pressing, embossing, rolling, casting, especially injection molding, or blowing, especially extrusion blowing, to give the semifinished product, finished product or end product.

In an alternative production process, a semifinished product, finished product or end product is at least partly, preferably fully (completely), coated with nanoparticles modified with an amphiphilic, preferably random copolymer, preferably with the copolymer-modified nanoparticles.

To coat the semifinished product, finished product or end product, it is especially possible to use a coating composition.

In principle, it is possible to coat interior and/or exterior surfaces of the semifinished product, finished product or end product.

With regard to further features and advantages of the process, reference is likewise made to the description above.

Finally, we provide a medical article, especially a medical, preferably surgical implant or a part thereof, comprising nanoparticles modified with an amphiphilic, preferably random copolymer or a polymer which comprises nanoparticles modified with an amphiphilic, preferably random copolymer.

Particularly preferably, the copolymer-modified nanoparticles are copolymer-modified nanoparticles, i.e., producible or obtainable by a process in which the nanoparticles are ablated by laser radiation from the surface of a substrate in a liquid comprising an amphiphilic, preferably random copolymer.

The abovementioned polymer is likewise preferably a polymer.

The copolymer-modified nanoparticles are present in the medical article preferably in homogeneous distribution or dispersion. Alternatively, the medical article may also have a coating with the copolymer-modified nanoparticles or the polymer. The coating may be formed on an interior and/or exterior surface of the medical article.

The nanoparticles, especially in the case of a purely surface coating of the medical article, may be released over a period of one week to 10 years, especially 6 weeks to 7 years, preferably 6 months to 3 years, to a physiological environment, especially after implantation of the article into the body of a patient to the body region surrounding the article.

The copolymer-modified nanoparticles preferably have a proportion of 0.01 to 50% by weight, especially 0.05 to 10% by weight, more preferably 0.05 to 5% by weight, especially 0.5 to 3% by weight, especially preferably 0.1 to 3% by weight, particularly 0.1 to 1% by weight, based on the total weight of the medical article.

The medical article may be formed from a polymer, preferably a fluorine-containing, fluorinated or fluorophilic polymer. For example, the medical article may be produced or made from a polymer selected from the group consisting of perfluoroxyalkyl vinyl ether, poly(chlorotri fluoroethylene), polyvinylidene difluoride, polytetrafluoroethylene, polyhexafluoropropylene, polytetrafluoroethylene, especially expanded polytetrafluoroethylene, homopolymers thereof, copolymers, in particular terpolymers, thereof and combinations or blends thereof.

Preferably, the medical article is selected from the group consisting of prosthesis, especially vascular prosthesis, stent, stent graft, stent lining, shunt, catheter, trocar, surgical instruments, cardiovascular implant, heart valve prosthesis, heart valve flaps, venous sheath, wound dressing, haemostatic, surgical suture material, anastomosis ring, medical meshes, especially hernia meshes, incontinence meshes and/or prolapse meshes, dental implant, epitheses and ortheses.

Particularly preferably, the medical article is a hollow implant, preferably a tubular implant, especially a vascular prosthesis, preferably an arterial vascular prosthesis. The tubular implant is preferably produced or made from polytetrafluoroethylene (PTFE), especially expanded polytetrafluoroethylene (ePTFE).

Particularly advantageously, the wall thickness of a medical article configured as a hollow implant is not influenced by the presence of the copolymer-modified nanoparticles. A medical article configured as a hollow implant preferably has a wall thickness of 0.05 to 1 mm, especially 0.2 to 0.8 mm, preferably 0.3 to 0.6 mm.

In addition, the medical article is preferably sterilized, especially with ethylene oxide.

With regard to further features and advantages of the medical article, especially in relation to the copolymer-modified nanoparticles, the nanoparticles themselves, the amphiphilic copolymer and possible polymers from which the article can be produced, reference is made completely to the description above.

We further provide a process for producing or manufacturing a medical article, in which nanoparticles modified with an amphiphilic, preferably random copolymer, preferably copolymer-modified nanoparticles, are incorporated into a raw polymer, and then the raw polymer is shaped together with the incorporated nanoparticles to give a medical article.

Especially preferably, the copolymer-modified nanoparticles are ablated by laser radiation from the surface of a substrate in a liquid comprising an amphiphilic, preferably random copolymer.

The raw polymer is preferably shaped together with the incorporated nanoparticles by extrusion, especially strand extrusion, film extrusion or fiber extrusion, spinning, especially fiber spinning, pressing, especially hot pressing, embossing, rolling, punch pressing, especially micro punch pressing, casting, especially injection molding, or blowing, especially extrusion blowing, to give the medical article.

An alternative production process for a medical article consists of at least partly, preferably fully (completely), coating an already prefabricated medical article with nanoparticles modified with an amphiphilic, preferably random copolymer, preferably with copolymer-modified nanoparticles.

In principle, both interior and exterior surfaces of the medical article can be coated with the copolymer-modified nanoparticles.

To coat the medical article, it is also possible to use a coating composition which comprises copolymer-modified nanoparticles. The coating composition may, for example, be a coating composition.

The copolymer-modified nanoparticles are also preferably incorporated into the raw polymer in the form of a liquid dispersion or of a masterbatch. For this purpose, preference is given to employing dispersions or masterbatches.

With regard to further features and advantages of the production processes for the medical article, reference is likewise made completely to the description above.

Advantages will be summarized once more hereinafter as follows.

The copolymer-modified nanoparticles exhibit essentially no agglomeration tendencies and are therefore outstandingly suitable for homogeneous incorporation into polymeric materials. Homogeneous distribution or dispersion of the copolymer-modified nanoparticles particularly advantageously brings about a likewise homogeneous development of the properties imparted thereby in the materials. Thus, with the copolymer-modified nanoparticles, medical articles in particular can be produced with homogeneously highly developed medical, especially diagnostic and/or therapeutic, properties.

The selection or production of the amphiphilic copolymer to be used for modification of the nanoparticles can be matched in a particularly advantageous manner to the polymers into which the copolymer-modified nanoparticles are to be incorporated. For example, preference is given to copolymers with fluorophilic side groups when the copolymer-modified nanoparticles are to be incorporated into fluorinated polymers, for example, polytetrafluoroethylene.

The amphiphilic copolymer-based modification of the nanoparticles is particularly advantageously sufficiently stable that it is not destroyed under the customary conditions of industrial shaping and forming processes, for example, extrusion processes.

Production of the copolymer-modified nanoparticles, which is based on laser ablation and simultaneous in situ functionalization or in situ conjugation of the laser-ablated nanoparticles with an amphiphilic, preferably random copolymer, also constitutes a high-purity operation. Complex and especially environmentally polluting purification and disposal steps are dispensed with.

A further advantage is that production of the copolymer-modified nanoparticles may not be dependent on chemical precursor compounds or stabilizers, thus yielding the copolymer-modified nanoparticles in a higher degree of purity. This is especially advantageous with respect to subsequent usage of the nanoparticles such as in semifinished products, finished products or end products, in particular medical articles.

A further advantage relates to the possibility to achieve a higher in situ functionalization or in situ conjugation of the laser-ablated nanoparticles with an amphiphilic, preferably random copolymer.

Depending on the type and number of substrates which are subjected to the laser ablation, it is possible in principle to produce more or less simultaneously copolymer-modified nanoparticles with different properties.

A further advantage relates to the possibility of what is called in-process control, for example, by UV-VIS spectroscopy, of the in situ functionalization of the laser-ablated nanoparticles.

A further advantage, finally, is also that there is no limitation whatsoever with regard to the nanoparticles. Instead, it is possible by laser ablation as a continuous operation to produce a desired amount or concentration of copolymer-modified nanoparticles.

Further features and advantages are evident from the description of preferred examples. In this context, individual features may each be implemented alone or in combination with others. The examples which follow are intended to illustrate in detail without restriction.

1. Materials and Analytical Methods

All reagents and solvents were purchased commercially, unless stated otherwise. 2-Ethylhexyl methacrylate (EHMA) and trimethylsilyl-2-hydroxyethyl methacrylate (TMS-HEMA) were dried over calcium chloride and distilled before use. 1H1H-Perfluorooctyl methacrylate (FOMA) was filtered through a column packed with active alumina. Poly(ethylene oxide)methacrylate (PEOMA, M approx. 360 g mol$^{-1}$) was used as obtained. Poly-p-hydroxystyrene was purchased from Polysciences, Inc. Varrington, Pa. ($M_w$=9000 to 11 000 g mol$^{-1}$–PDI about 3).

NMR analyses were conducted on a Bruker 250 or 300 MHz spectrometer. Gel permeation chromatography was conducted at 30° C. using MZ-Gel SDplus 10E6, 10E4 and 500 columns, an ERC RI-101 differential refractometer detector, and THF as an eluent.

Transmission electron micrographs were obtained by a Technai F20 microscope. The samples were prepared by ultramicrotomy.

Dynamic light scattering measurements were conducted by an ALV 5000 correlator, ALV-SP81 goniometer laser (krypton ion laser 647.1 nm—Spektra Physics Model Kr2025—avalanche photodiode module).

2. Preparation of Amphiphilic Random Copolymers 2.1. Preparation of an Amphiphilic Random Copolymer of the Formula III Below Formula III

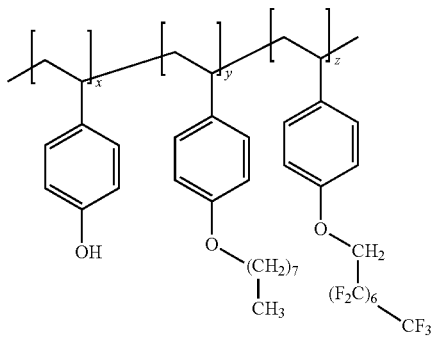

Copolymer III was prepared by substitution of poly(p-hydroxystyrene) with 1-octyl bromide and 1H,1H-perfluorooctyl bromide. In the copolymer obtained, 50 mol % of the monomer units had an n-octyl side chain in the p position, and 15 mol % of the monomer units a 1H,1H-perfluorooctyl unit.

2.2. Preparation of an Amphiphilic Random Copolymer of the Formula IV Below

Formula IV

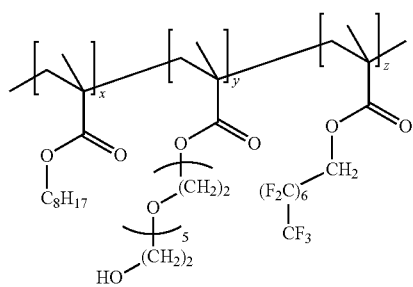

Copolymer IV was prepared by a free-radical polymerization of 2.6 mmol of EHMA, 0.4 mmol of PEOMA and 1.3 mmol of FOMA in 11.5 ml of 1,4-dioxane in the presence of 0.03 mmol of AIBN as an initiator at 65° C. over 16 hours. Subsequently, the product was precipitated twice in methanol and then dried under reduced pressure. The resulting copolymer with the Formula IV had a molecular weight $M_n$=45900 g/mol$^{-1}$ (PDI=1.9) with 58 mol % of EHMA, 7 mol % of PEOMA and 35 mol % of PFOMA.

3. Preparation of Matrix Polymers 3.1. Preparation of poly(2,3,4,5,6-pentafluorostyrene) (PFS)

PFS was prepared by a free-radical polymerization of 1 ml of 2,3,4,5,6-pentafluorostyrene in 1 ml of THF at 60° C. over 5 hours in the presence of $1.8 \times 10^{-5}$ mol of AIBN as an initiator. Subsequently, the product was precipitated twice in methanol and dried under reduced pressure.

3.2. Preparation of poly(1H,1H-heptafluorobutyl methacrylate) (PFBA)

PFBA was prepared by a polymerization of 3.1 mmol of 1H,1H-heptafluorobutyl methacrylate in the presence of $1.3 \times 10^{-5}$ mol of AIBN as initiator. Polymerization was conducted at 70° C. over one hour. Subsequently, the product was precipitated twice in methanol and dried under reduced pressure.

4. Production of Copolymer-Modified Nanoparticles

Generation of nanoparticles was conducted by a nanosecond laser system (New wave Gemini PIV) which provided laser pulses with a pulse duration of 3 to 5 nanoseconds at a central wavelength of 532 nm. The laser system generated laser pulses with a pulse energy of up to 0.1 joule with a repetition rate of 15 Hz. The laser beam was focussed through focussing lenses (focal length 40 mm) onto the surfaces of a silver and copper substrate. All experiments were conducted with a pulse energy of 7 mJ and with a 1 mm offset of the substrates in relation to the focus.

The silver and copper substrates were each placed separately onto the base of a sample vessel. Subsequently, the sample vessels were each filled with 2 ml of a solution containing THF and one of the copolymers prepared under 2, such that the substrates were in each case fully immersed into the solution.

In this way, the copolymers were present during generation of copper and silver nanoparticles and brought about in situ functionalization of the nanoparticles during generation thereof.

The nanoparticles generated in the THF solution were characterized by dynamic light scattering (DLS) and transmission electron microscopy (TEM) and energy-dispersive x-ray spectroscopy (EDX). The dispersions obtained after conducting the laser ablation did not result in signs of precipitation. In addition, conduction of the abovementioned methods for characterization of the nanoparticles generated by laser ablation showed that they were present coated with the copolymer and hence separately from one another, as a result of which flocculation, precipitation or sedimentation tendencies were successfully suppressed.

5. Incorporation of the Copolymer-Modified Nanoparticles Into Polymers

For incorporation of nanoparticles produced under 4, the matrix polymers PFS and PFBA were selected. For this purpose, 10 mg in each case of the matrix polymer were dissolved in 1 ml of THF. Subsequently, 0.8 ml of the dispersion produced as under 4. was added. The resulting mixture was heated to 55° C. over one hour. Subsequently, the THF solvent was removed under reduced pressure.

6. Production of an ePTFE Prosthesis with Copolymer-Modified Nanoparticles

Pure PTFE powder was used to produce a pasty, PTFE-containing dispersion by addition of a liquid lubricant, for example, of odorless petroleum spirit or naphtha. This dispersion was admixed with copolymer-modified silver nanoparticles according to Example 4 and homogenized by stirring. The concentration of the copolymer-modified nanoparticles used was 1.0% by weight, based on the total weight of the PTFE used. The homogeneous mixture obtained was then preshaped to a cylindrical blank with a pressure of 3000 kPa (kilopascals). The preshaped blank was then extruded to a tube with an internal diameter of 6 mm. The resulting extrudate was expanded at a temperature of 325° C. and converted to a tubular shape. Subsequently, the extrudate was sintered above the expansion temperature at 350° C. to crystallize the extruded structure. Finally, the extruded prosthesis was rinsed to remove adhering non-integrated copolymer-modified silver nanoparticles. Finally, the prosthesis was cut to the desired length.

The invention claimed is:

1. A random copolymer comprising hydrophilic, fluorophilic, and hydrophobic side groups of Formula III:

Formula III

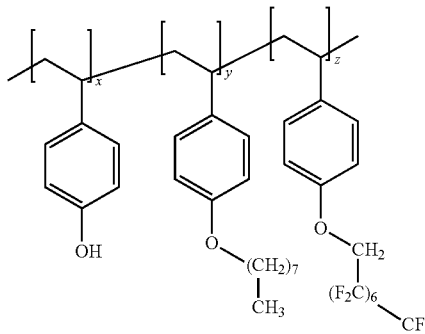

where x, y and z are each a molar proportion of monomer units in the copolymer.

2. A random copolymer comprising hydrophilic, fluorophilic, and hydrophobic side groups of Formula III:

Formula IV

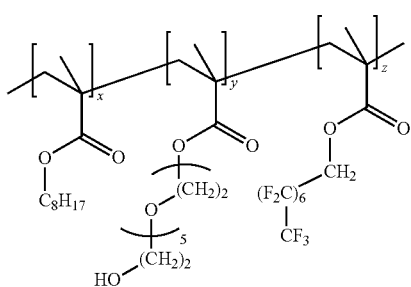

where x, y and z are each a molar proportion of monomer units in the copolymer.

3. The random copolymer of claim 1, which is prepared by substituting poly(p-hydroxystyrene) with 1-octyl bromide and 1H,1H-perfluorooctyl bromide.

4. The random copolymer of claim 1, wherein 50 mol % of the monomer units comprise an n-octyl side chain and 15 mol % of the monomer units comprise a 1H,1H-perfluorooctyl side chain.

5. The random copolymer of claim 2, which is prepared by free-radical polymerization of 2-ethylhexyl methacrylate (EHMA), 1H,1H-perfluorooctyl methacrylate (FOMA), and poly(ethylene oxide)methacrylate (PEOMA).

6. The random copolymer of claim 5, which is prepared with 58 mol % of EHMA, 7 mol % of PEOMA, and 35 mol % of PFOMA.

7. The random copolymer of claim 2, wherein the polymer has a number average molecular weight of 45900 grams per mole.

8. The random copolymer of claim 7, wherein the polymer has a polydispersity index of 1.9.

9. A method of preparing the random copolymer of claim 1 comprising:
   providing poly(p-hydroxystyrene); and
   substituting the poly(p-hydroxystyrene) with 1-octyl bromide and 1H,1H-perfluorooctyl bromide.

10. A method of preparing the random copolymer of claim 2, comprising:
    providing 2-ethylhexyl methacrylate (EHMA), 1H,1H-perfluorooctyl methacrylate (FOMA), and poly(ethylene oxide)methacrylate (PEOMA);
    dissolving EHMA, FOMA, and PEOMA in 1,4-dioxane in the presence of azobisisobutyronitrile (AIBN);
    heating at 65° C. for over 16 hours to form a random copolymer;
    precipitating the product of the previous step twice in methanol; and
    drying under reduced pressure.

* * * * *